(12) United States Patent
Nolting

(10) Patent No.: US 7,540,880 B2
(45) Date of Patent: Jun. 2, 2009

(54) DIFFERENTIALLY COATED STENT

(75) Inventor: John Nolting, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 170 days.

(21) Appl. No.: 11/555,845

(22) Filed: Nov. 2, 2006

(65) Prior Publication Data

US 2007/0061007 A1 Mar. 15, 2007

Related U.S. Application Data

(63) Continuation-in-part of application No. 10/350,704, filed on Jan. 24, 2003, now abandoned.

(51) Int. Cl.
*A61F 2/06* (2006.01)
(52) U.S. Cl. ...................... 623/1.15; 623/901
(58) Field of Classification Search ........ 623/1.42–1.48
See application file for complete search history.

(56) References Cited

U.S. PATENT DOCUMENTS

| | | | |
|---|---|---|---|
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau et al. | |
| 5,464,650 A | 11/1995 | Berg et al. | |
| 6,090,127 A | 7/2000 | Globerman | |
| 7,344,560 B2* | 3/2008 | Gregorich et al. | 623/1.15 |
| 2003/0050689 A1 | 3/2003 | Matson | |
| 2003/0139801 A1* | 7/2003 | Sirhan et al. | 623/1.15 |
| 2004/0106975 A1 | 6/2004 | Solovay et al. | |
| 2007/0027530 A1* | 2/2007 | Saint et al. | 623/1.42 |
| 2008/0086195 A1* | 4/2008 | Atanasoka et al. | 623/1.15 |

* cited by examiner

*Primary Examiner*—Suzette J Gherbi

(57) ABSTRACT

A stent is differentially coated to accommodate areas of high strain. A therapeutic coating is applied to only those areas of the stent that do not experience high strain. This allows a therapeutic coating to be chosen for its elution characteristics, for example, rather than for its ability to withstand high strain. An elastic coating may be applied to the areas of high strain. The elastic coating may or may not include a therapeutic agent.

20 Claims, 5 Drawing Sheets

500

DIFFERENTIALLY COATED STENT

RELATED APPLICATIONS

This application is a continuation-in-part of U.S. patent application Ser. No. 10/350,704 filed Jan. 24, 2003 now abandoned and claims the benefit of that application. The entirety of that application is incorporated herein by reference.

TECHNICAL FIELD

This invention relates generally to biomedical stents. More specifically, the invention relates to stents that are differentially coated to accommodate areas of high strain.

BACKGROUND OF THE INVENTION

Stents are cylindrical-shaped devices that are radially expandable to hold open a segment of a vessel or other anatomical lumen after implantation into the body lumen. Various types of stents are in use, including expandable and self-expanding stents. Expandable stents generally are conveyed to the area to be treated on balloon catheters or other expandable devices. For insertion, the stent is positioned in a compressed configuration along the delivery device, for example crimped onto a balloon that is folded or otherwise wrapped about a guide wire that is part of the delivery device. After the stent is positioned across the lesion, it is expanded by the delivery device, causing the length of the stent to contract and the diameter to expand. For a self-expanding stent, commonly a sheath is retracted, allowing expansion of the stent.

Stents are used in conjunction with balloon catheters in a variety of medical therapeutic applications, including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion, thereby increasing the inner diameter of the affected vessel. The increased interior vessel diameter facilitates improved blood flow.

Soon after the procedure, however, a significant proportion of treated vessels restenose. To prevent restenosis, short flexible cylinders, or stents, constructed of metal or various polymers, are implanted within the vessel to maintain lumen size. The stents act as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau.

Stent insertion may cause undesirable reactions such as inflammation, infection, thrombosis, and proliferation of cell growth that occludes the passageway. Stents have been used with coatings to deliver drugs or other therapeutic agents at the site of the stent that may assist in preventing these conditions. The coatings must be bioengineered to control the release of highly potent and potentially toxic drugs.

The choice of a coating may be limited by its mechanical attributes. For example, a polymer with a desired drug elution profile may be brittle and prone to cracking in areas of the stent that experience high strain while the stent is being compressed during manufacture or expanded during delivery into the target vessel. Alternatively, a coating that erodes at a desired rate, thereby delivering drug at a known, controlled rate, may also be brittle or otherwise unable to withstand the strains of compression or expansion. Cracking of a coating in high-strain areas may cause extensive delamination of the coating from other areas of the stent, resulting in an unknown amount of drug being delivered.

Therefore it would be desirable to have an improved, differentially coated stent that accommodates these areas of high strain and overcomes the above and other disadvantages.

SUMMARY OF THE INVENTION

One aspect of the present invention is a system for treating a vascular condition, comprising a catheter; a stent coupled to the catheter, the stent including a stent framework, the stent framework including areas of high strain; and a therapeutic coating disposed on the stent framework and avoiding the areas of high strain. The system may further comprise an elastic coating disposed on at least the high strain areas of the stent framework.

Another aspect of the present invention is a coated stent having a stent framework, the stent framework including areas of high strain, and a therapeutic coating disposed on at least a portion of the stent framework and avoiding the areas of high strain. The stent may further comprise an elastic coating disposed on at least the areas of high strain.

Yet another aspect of the present invention is a method of manufacturing a differentially coated stent. A stent framework is provided, the stent framework including areas of high strain. A therapeutic coating is applied to at least a portion of the stent framework, avoiding the areas of high strain. An elastic coating may be applied to at least the high-strain areas of stent framework either before or after the therapeutic coating is applied.

An additional aspect of the present invention is a system for producing a differentially coated stent, comprising means for providing a stent framework, the stent framework including areas of high strain, and means for applying a therapeutic coating to at least a portion of the stent framework, avoiding the areas of high strain. The system may further comprise means for applying an elastic coating to at least the areas of high strain The aforementioned, and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
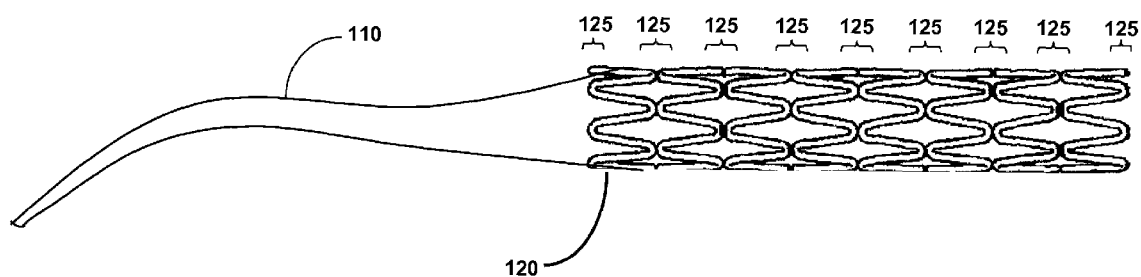
FIG. 1 is an illustration of one embodiment of a system for treating a vascular condition, in accordance with the present invention.

One aspect of the present invention is a system for treating a vessel. One embodiment of the system, in accordance with the present invention, is illustrated in FIG. 1 at 100. System 100 comprises a catheter 110 and a stent 120 coupled to the catheter. Stent 120 includes a stent framework with areas of high strain 125. Stent 120 is differentially coated, with a therapeutic coating disposed on at least a portion of the stent framework and avoiding the areas of high strain. An elastic coating may be disposed on the areas that experience high strain.

Catheter 110 may include a balloon to expand the stent, or it may include a sheath that retracts to allow expansion of a self-expanding stent. Both types of catheter are well known in the art. Stent 120 is shown coupled to catheter 110 for delivery within a vessel.

The stent framework may be made of a wide variety of medical implantable materials, such as stainless steel, nitinol, tantalum, ceramic, nickel, titanium, aluminum, polymeric materials, MP35N, stainless steel, titanium ASTM F63-83 Grade 1, niobium, high carat gold K 19-22, or combinations of the above.

Areas of high strain 125 may be those areas of the stent framework that undergo deformation, for example when a stent is compressed onto a delivery catheter during manufacture or expanded during delivery. Coatings on high-strain areas of the stent framework may experience the same high strain as the stent framework. For this reason, these high-strain areas may be left uncoated or may be coated with an elastic coating that is capable of withstanding high strain without cracking, delaminating, or otherwise failing. Areas of the stent framework that do not experience high strain are coated with a therapeutic coating that may be selected for characteristics such as elution profile or durability rather than an ability to withstand high strain.

The therapeutic coating may include a therapeutic agent such as an antineoplastic agent, an antiproliferative agent, an antibiotic, an antithrombogenic agent, an anticoagulant, an antiplatelet agent, an anti-inflammatory agent, combinations of the above, and the like. The coating may be a polymer, including, but not limited to, urethane, polylactide (PLA), poly-l-lactic acid (PLLA), polyglycolic acid (PGA) polymer, poly (e-caprolactone) (PCL), polyacrylates, polymethacrylates, polycaprolactone (PCL), polymethylmethacrylate (PMMA), combinations and/or copolymers of the above, and the like. The specific polymer, polymer combinations or copolymers used may be adjusted as seen fit as required by the specific needs of the medical device and the drug used. The therapeutic coating can be applied to the stent or a portion of the stent in a variety of methods such as, for example, pad printing, inkjet printing, rolling, painting, spraying, microspraying, dipping, wiping, electrostatic deposition, vapor deposition, epitaxial growth, and combinations thereof.

The elastic coating may be a polymer, including, but not limited to, urethane, polycaprolactone (PCL), polybutylmethacrylate (PBMA), polyethylenevinyl acetate (PEVA), combinations and/or copolymers of the above, and the like. The specific polymer, polymer combinations or copolymers used may be adjusted as required by the specific needs of the medical device and the drug used. The elastic coating may comprise a different polymer than that comprising the therapeutic coating. The elastic coating may include no therapeutic agent, or it may include a therapeutic agent that is the same as or different from the agent carried in the therapeutic coating. The elastic coating can be applied to the stent or a portion of the stent in a variety of methods such as, for example, pad printing, inkjet printing, rolling, painting, spraying, microspraying, dipping, wiping, electrostatic deposition, vapor deposition, epitaxial growth, and combinations thereof.

Using the same therapeutic agent in both coatings may offer the benefit of delivering the therapeutic agent at different rates or different times. For example, the two coatings may display different elution characteristics, resulting in a drug being delivered at two rates; or they may have different durability characteristics, allowing the drug to be delivered by elution from one coating and being released through erosion from another. If the coatings contain different therapeutic agents, a benefit may be realized from the ability to simultaneously deliver more than one therapeutic agent.

Figure 2:
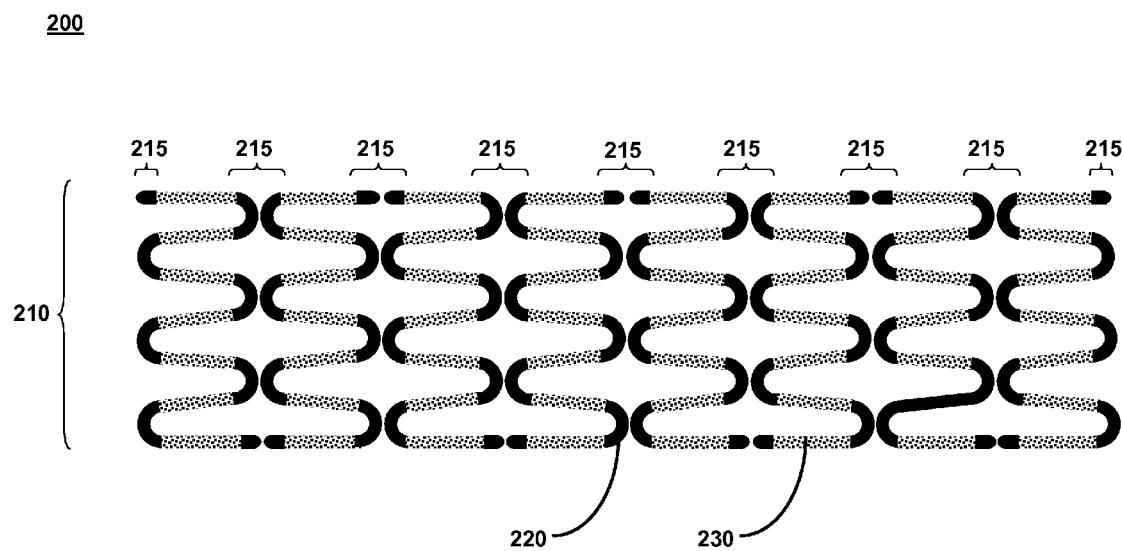
FIG. 2 is an illustration of one embodiment of a differentially coated stent, in accordance with the present invention.

Another aspect of the present invention is a differentially coated stent. One embodiment of the stent, in accordance with the present invention, is illustrated in FIG. 2 at 200. Stent 200 includes a stent framework 210 with areas of high strain 215. Stent 200 is differentially coated, with an elastic coating 220 disposed on the areas that experience high strain and a therapeutic coating 230 disposed on areas that experience low or no strain. Alternatively, the stent may be uncoated in the areas that experience high strain.

Stent framework 210 may be made of a wide variety of medical implantable materials, such as stainless steel, nitinol, tantalum, ceramic, nickel, titanium, aluminum, polymeric materials, MP35N, stainless steel, titanium ASTM F63-83 Grade 1, niobium, high carat gold K 19-22, or combinations of the above.

Areas of high strain 215 may be those areas of the stent framework that undergo deformation, for example when the stent is compressed onto a delivery catheter during manufacture or expanded during delivery. Coatings on high-strain areas of the stent framework may experience the same high strain as the stent framework. For this reason, these high-strain areas may be left uncoated or may be coated with an elastic coating 220 that is capable of withstanding high strain without cracking, delaminating, or otherwise failing. Areas of the stent framework that do not experience high strain are coated with a therapeutic coating 230. Elastic coating 220 and therapeutic coating 230 may comprise different polymers with different material properties. Because the therapeutic coating is not exposed to high strain, it may be selected for characteristics such as elution profile or durability rather than the ability to withstand high strain.

Therapeutic coating 230 may include a therapeutic agent such as an antineoplastic agent, an antiproliferative agent, an antibiotic, an antithrombogenic agent, an anticoagulant, an antiplatelet agent, an anti-inflammatory agent, combinations of the above, and the like. The coating may be a polymer, including, but not limited to, urethane, polycaprolactone (PCL), polymethylmethacrylate (PMMA), combinations of the above, and the like.

Elastic coating 220 may be a polymer, including, but not limited to, urethane, polycaprolactone (PCL), polybutylmethacrylate (PBMA), combinations of the above, and the like. The elastic coating may include no therapeutic agent, or it may include a therapeutic agent that is the same as or different from the agent carried in the therapeutic coating. Using the same therapeutic agent in both coatings may offer the benefit of delivering the therapeutic agent at different rates or different times. For example, the two coatings may display different elution characteristics, resulting in a drug being delivered at two rates; or they may have different durability characteristics, allowing the drug to be delivered by elution from one coating and being released through erosion from another. If the coatings contain different therapeutic agents, a benefit may be realized from the ability to simultaneously deliver more than one therapeutic agent.

Figure 3:
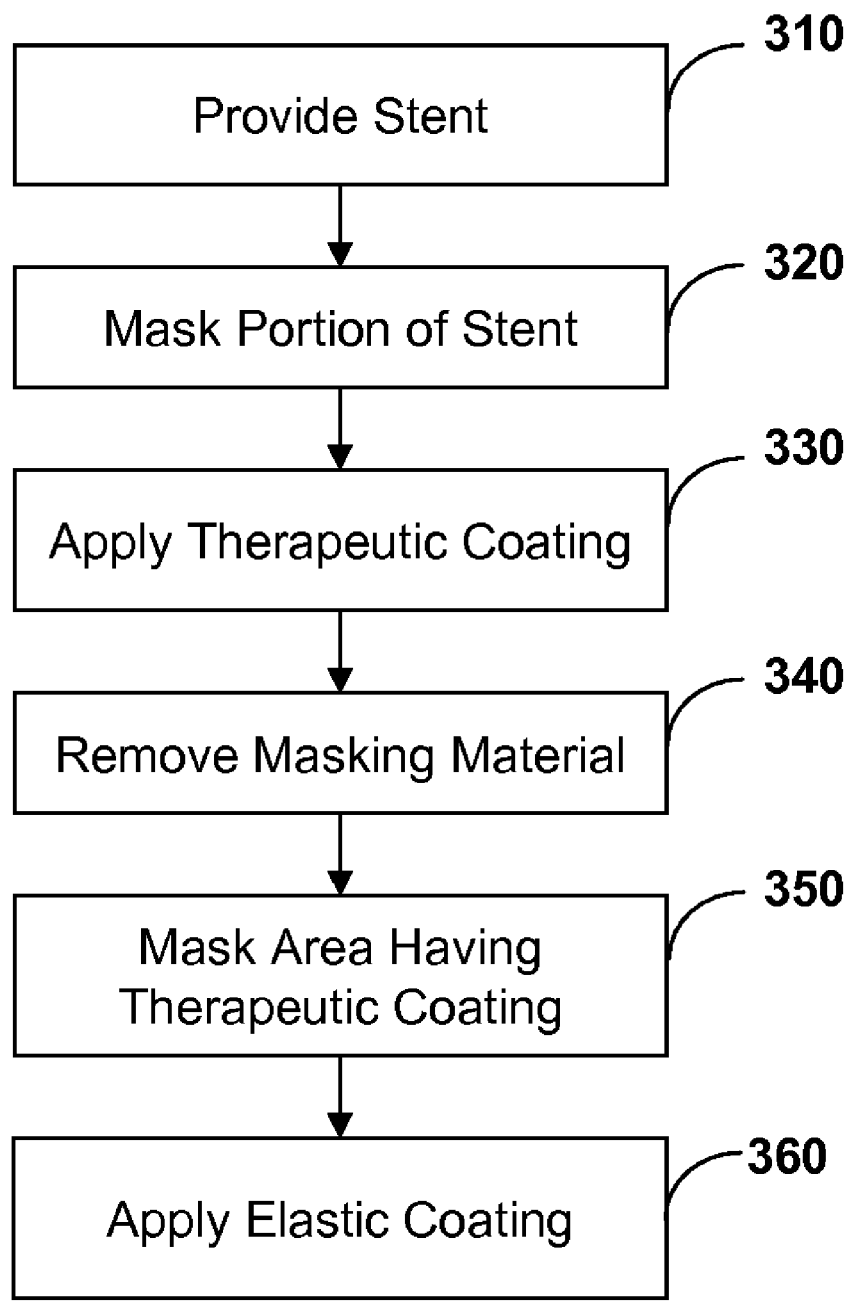
FIG. 3 is a flow diagram of one embodiment of a method of manufacturing a differentially coated stent, in accordance with the present invention.

A further aspect of the present invention is a method of manufacturing a differentially coated stent. FIG. 3 shows a flow diagram of one embodiment, in accordance with the present invention at 300.

In this embodiment, a stent framework is provided (Block 310). High-strain areas of the stent framework are masked by, for example, applying a narrow tetrafluorethylene sleeve over each area (Block 320). High-strain areas of the stent framework also may be masked by applying an adhesive-backed material and/or applying a removable polymeric coating. A therapeutic coating is then sprayed onto or otherwise applied to the stent framework, avoiding the areas of high strain (Block 330). The masking material is removed (Block 340). The areas carrying the therapeutic coating are then masked (Block 350), and an elastic coating is sprayed onto or otherwise applied to the areas of high strain (Block 360). The areas carrying the therapeutic coating may be masked by applying a narrow tetrafluorethylene sleeve, an adhesive-backed material and/or applying a removable polymeric coating over each area to be masked. Those skilled in the art will recognize that the high-strain areas may also be left uncoated.

Figure 4:
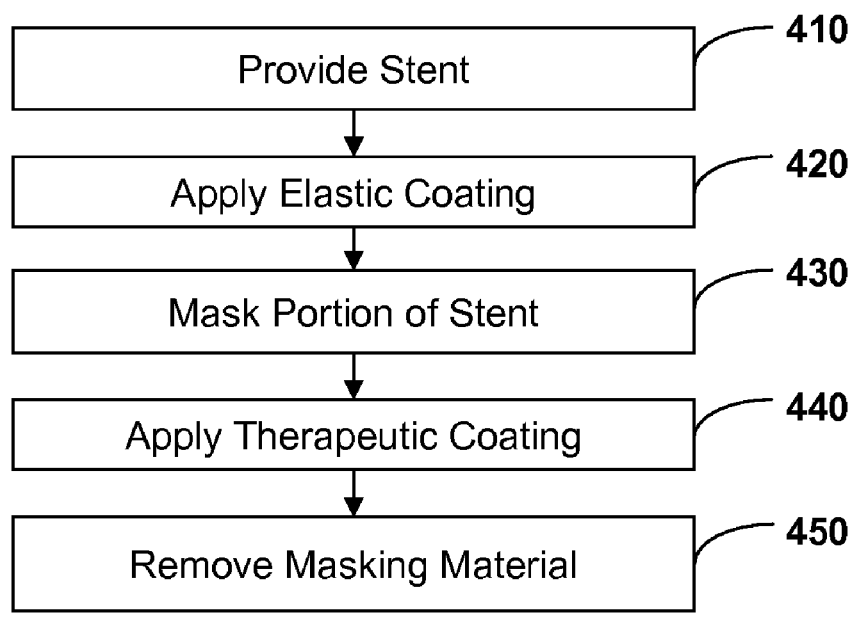
FIG. 4 is a flow diagram of another embodiment of a method of manufacturing a differentially coated stent, in accordance with the present invention.

FIG. 4 shows a flow diagram of another embodiment of a method of manufacturing a differentially coated stent, in accordance with the present invention at 400.

In this embodiment, a stent framework is provided (Block 410). The stent framework is coated with an elastic coating (Block 420). High-strain areas of the stent framework are then masked by, for example, applying a narrow tetrafluorethylene sleeve over each area (Block 430). High-strain areas of the stent framework also may be masked by applying an adhesive-backed material and/or applying a removable polymeric coating. A therapeutic coating is then sprayed onto or otherwise applied to the stent framework, avoiding the areas of high strain (Block 440). After coating, the masking material is removed (Block 450).

Figure 5:
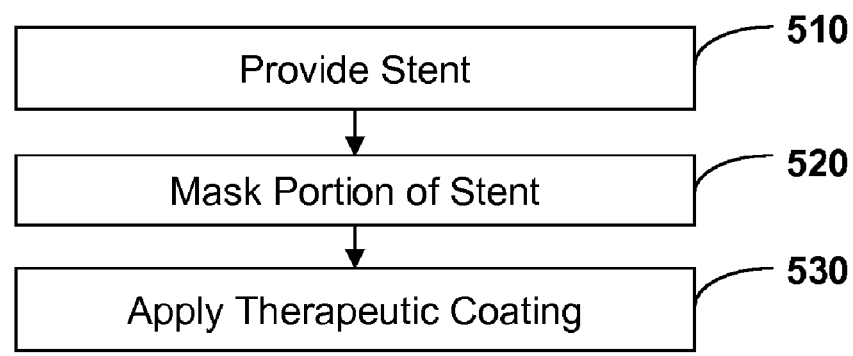
FIG. 5 is a flow diagram of another embodiment of a method of manufacturing a differentially coated stent, in accordance with the present invention.

FIG. 5 shows a flow diagram of yet another embodiment of a method of manufacturing a differentially coated stent, in accordance with the present invention at 500.

A stent framework is provided (Block 510). High-strain areas of the stent framework are masked by coating with a protective polymer coating material such as Parylene (Block 520). The stent framework is then dipped into or otherwise exposed to a therapeutic coating (Block 530). The protective polymer coating material resists the therapeutic coating, resulting in the high-strain areas being coated with only the protective polymer.

While the embodiments of the invention disclosed herein are presently considered preferred, various changes and modifications can be made without departing from the spirit and scope of the invention. The scope of the invention is indicated in the appended claims, and all changes and modifications that come within the meaning and range of equivalents are intended to be embraced therein.

The invention claimed is:

1. A method of manufacturing a differentially coated stent, comprising:

providing a stent framework, the stent framework including areas of high strain;

masking the high strain areas of the stent framework;

applying a therapeutic coating to the unmasked stent framework;

removing the mask from the masked high strain areas of the stent framework;

masking the areas of the stent framework having the therapeutic coating; and applying an elastic coating to the unmasked high-strain areas of the stent framework.

2. The method of claim 1 wherein the high strain areas of the stent framework are masked by one or more materials selected from a group consisting of a tetrafluorethylene sleeve, an adhesive-backed material, and a removable polymeric coating.

3. The method of claim 1 wherein the therapeutic coating is applied by a method selected from the group consisting of pad printing, inkjet printing, rolling, painting, spraying, microspraying, dipping, wiping, electrostatic deposition, vapor deposition, epitaxial growth, and combinations thereof.

4. The method of claim 1 wherein the elastic coating is applied by a method selected from the group consisting of pad printing, inkjet printing, rolling, painting, spraying, microspraying, dipping, wiping, electrostatic deposition, vapor deposition, epitaxial growth, and combinations thereof.

5. The method of claim 1 wherein the therapeutic coating comprises a first polymer and the elastic coating comprises a second polymer.

6. The method of claim 1 wherein the therapeutic coating includes a therapeutic agent selected from a group consisting of an antineoplastic agent, an antiproliferative agent, an antibiotic, an antithrombogenic agent, an anticoagulant, an antiplatelet agent, and an anti-inflammatory agent.

7. The method of claim 1 wherein the elastic coating includes a therapeutic agent selected from a group consisting of an antineoplastic agent, an antiproliferative agent, an antibiotic, an antithrombogenic agent, an anticoagulant, an antiplatelet agent, and an anti-inflammatory agent.

8. The method of claim 7 wherein the therapeutic coating and the elastic coating display different elution characteristics.

9. The method of claim 1 wherein the therapeutic coating includes a first therapeutic agent and the elastic coating includes a second therapeutic agent.

10. The method of claim 9 wherein the therapeutic coating and the elastic coating display different elution characteristics.

11. The method of claim 1 wherein the therapeutic coating and the elastic coating display different durability characteristics.

12. The method of claim 1 wherein the elastic coating is a polymer selected from a group consisting of, urethane, polycaprolactone (PCL), polybutylmethacrylate (PBMA), polyethylenevinyl acetate (PEVA), combinations and/or copolymers of the above.

13. A differentially coated stent, the stent comprising:

a stent framework, the stent framework including a plurality of high strain areas and a plurality of low strain areas, each low strain area adjacent to at least one high strain area;

an elastic coating disposed on each of the plurality of high strain areas; and a therapeutic coating disposed on each of the plurality of low strain areas.

14. The stent of claim 13 wherein the therapeutic coating includes a therapeutic agent selected from a group consisting of an antineoplastic agent, an antiproliferative agent, an antibiotic, an antithrombogenic agent, an anticoagulant, an antiplatelet agent, and an anti-inflammatory agent.

15. The stent of claim 13 wherein the elastic coating includes a therapeutic agent, the therapeutic agent selected from a group consisting of an antineoplastic agent, an antiproliferative agent, an antibiotic, an antithrombogenic agent, an anticoagulant, an antiplatelet agent, and an anti-inflammatory agent.

16. The stent of claim 15 wherein the therapeutic coating and the elastic coating display different elution characteristics.

17. The stent of claim 15 wherein the therapeutic coating includes a first therapeutic agent and the elastic coating includes a second therapeutic agent, the first therapeutic agent different than the second therapeutic agent.

18. The stent of claim 17 wherein the first therapeutic agent of the therapeutic coating and the second therapeutic agent of the elastic coating display different elution characteristics.

19. The stent of claim 13 wherein the therapeutic coating and the elastic coating display different durability characteristics.

20. The stent of claim 13 wherein the elastic coating is a polymer selected from a group consisting of, urethane, polycaprolactone (PCL), polybutylmethacrylate (PBMA), polyethylenevinyl acetate (PEVA), combinations and/or copolymers of the above.

* * * * *